United States Patent [19]
Braun et al.

[11] 3,960,859
[45] June 1, 1976

[54] 21-DEOXYDIHYDROAJMALINE DERIVATIVES

[75] Inventors: Klaus Braun; Günther Gabsch, both of Radebeul; Werner Förster, Halle; Rolf Ertel, Dresden; Klaus Femmer, Radebeul, all of Germany

[73] Assignee: VEB Arzneimittelwerk Dresden, Radebeul, Germany

[22] Filed: Mar. 20, 1975

[21] Appl. No.: 560,270

Related U.S. Application Data

[63] Continuation of Ser. No. 373,557, June 25, 1973, abandoned, which is a continuation of Ser. No. 90,472, Nov. 17, 1970, abandoned.

[52] U.S. Cl. .................. 260/247.5 FP; 260/293.55; 424/248; 424/267
[51] Int. Cl.² ........................................ C07D 471/08
[58] Field of Search ............. 260/247.5 FP, 293.55; 424/248, 267

[56] References Cited
OTHER PUBLICATIONS
E. Bombardelli et al., Chemical Abstracts vol. 60, p. 12068, (1964).
A. Bonati et al., Chemical Abstracts vol. 60, p. 5576, (1964).

Primary Examiner—Alton D. Rollins
Assistant Examiner—Jose Tovar
Attorney, Agent, or Firm—Nolte and Nolte

[57] ABSTRACT

Novel 21-deoxydihydroajmaline derivatives having the formula

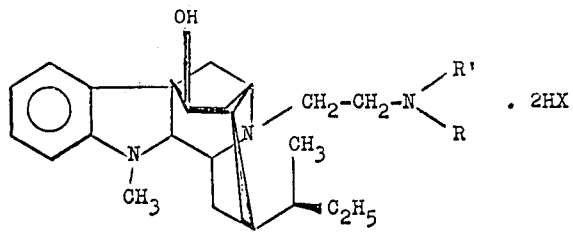

wherein R and R' are each the same alkyl group of 2 to 4 carbon atoms or R and R' together with the N atom with which they are associated form a saturated 5- or 6- atom ring, the atoms other than the nitrogen atom of which are all carbon atoms or one oxygen atom and the rest carbon atoms and X is the anion of a physiologically inorganic or organic acid, characterized by their antiarhythmic activity.

10 Claims, No Drawings

21-DEOXYDIHYDROAJMALINE DERIVATIVES

This is a continuation of application Ser. No. 373,557 filed June 25, 1973, which in turn is a continuation of Ser. No. 90,472, filed Nov. 17, 1970, both now abandoned.

This invention relates to a novel series of 21-deoxydihydroajmaline derivatives having advantageous pharmalogical properties and to methods of preparing and using the same.

More particularly, this invention relates to 21-deoxydihydroajmaline derivatives having the formula

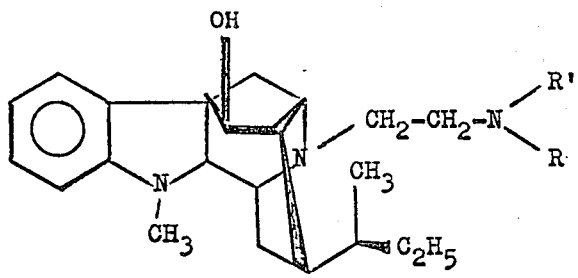 · 2HX wherein R and R' are each the same alkyl group of 3 to 4 carbon atoms or R and R' together with the N atom with which they are associated form a saturated 5- or 6-atom ring, the atoms other than the nitrogen atom of which are all carbon atoms or one oxygen atom and the rest carbon atoms and X is the anion of a physiologically acceptable inorganic or organic acid which derivatives are characterized by their antiarhythmic activity.

The rauwolfiaalkaloid ajmalin has been used for over 10 years as a therapeutic agent because of its valuable antiarhythmic properties. If the compound ajmalin is reduced according to the method of Huang-Minlon (J. Chem. Soc. (London) 1954, pages 1242–1260), ring splitting takes place to form 21-deoxydihydroajmaline and the rhythm regulating activity is extensively lost.

It has now been found that through the substitution of the secondary amino group of the 21-deoxydihydroajmaline to form the corresponding amino ethyl halogenide compound, the antiarhythmic activity of ajmalin is restored and in fact is far surpassed.

The novel compounds of the invention are prepared by reacting 21-deoxydihydroajmaline with a basically substituted ethyl halogenide advantageously in the presence of an alcohol or cyclic ether and preferably at the boiling point of such solvent and then converting the resultant free base into the corresponding salt by reaction with an inorganic or organic acid. The acid can be any pharmaceutically acceptable acid, as for instance, hydrochloric, hydrobromic, phosphoric, sulfuric, tartaric, acetic, oxalic, citric acid and the like.

The novel compounds of the invention were evaluated in animal experiments and demonstrated up to a nine-fold stronger antiarhythmic activity than the known ajmaline. In addition, the compounds demonstrated in the Langendorff heart procedures a coronary vessel dilating effect.

In the table which follows, the results of the aconitine test procedures carried out in rats for comparing the activities of the compounds of the invention and the known compounds ajmaline and N-propylajmaline (DBP 1,196,207; DBP 1,154,120) have been set out. In the procedures the term $ED_{20}$ designates the dose in mg/kg at which only isolated or sporadic ventricular extrasystoles occur.

Table 1

| Compound | $ED_{20}$ | $LD_{50}$ | Q |
|---|---|---|---|
| Example 3 | 0.25 | 5.4 | 21.6 |
| Ajmaline | 2.13 | 26.0 | 12.2 |
| N-Propylajmaline | 0.17 | 1.4 | 8.2 |

As can be seen from the Table, the rhythm regulating activity of the compound of the invention is considerably increased as compared to ajmaline and, furthermore, the therapeutic range in the case of the compound of the invention as compared to the known similarly active N-propylajmaline is increased almost threefold.

In connection with the fibrillation or flutter generated by aconitine in the dog, the compound according to Example 3, i.e., 4-(β-piperidinoethyldeoxydihydroajmaline-dihydrochloride) in a dose of 0.6 mg/kg has about the same therapeutic effectiveness as N-propylajmaline administered in a dose of 0.3 mg/kg, however, the administration of a compound of the invention produces no side effects while the N-propylajmaline produced undesirable side effects in at least 30% of the cases to which it is administered.

The following Examples are given for the purpose of illustrating the invention and are not in any way to be construed as limiting the scope thereof.

EXAMPLE 1

3.12g 21-Deoxydihydroajmaline were dissolved in 50 ml absolute dioxane and the solution heated to boiling together with 1.65 g β-diethyl amino ethyl chloride for nine hours. The reaction solution was evaporated to dryness under vacuum and the residue taken up in soda solution and ether. The ether extract was dried over $Na_2SO_4/K_2CO_3$ and then introduced into a column containing 100 g $Al_2O_3$. The column was thereafter eluted with ether or dioxane. The dried residue of the eluate was taken up in absolute ether and reacted with an excess of etheric hydrochloric acid. The colorless hygroscopic precipitate was separated off by $N_2$ pressure filtration and dried in a vacuum desiccator. 4-(β-Diethylaminoethyl)-deoxydihydroajmaline-dihydrochloride having a melting point of 146°–150°C (decomp.) was recovered in a yield of 77%. $[\alpha]_D^{20} +35°$ (ethanol).

EXAMPLE 2

3.12 g 21-Deoxydihydroajmaline in 80 ml ethanol were reacted with 2g β-morpholinoethylchloride for 16 hours under reflux and further worked up as described in Example 1.

4-(β-Morpholinoethyl)-deoxydihydroajmaline-dihydrochloride was recovered in a yield of 67% in the form of colorless crystals having a melting point of 140°–146°C (decomp.). $[\alpha]_D^{20} = +37°$.

In the same manner the following compounds were prepared:

| Example No. | R | X | M.P. °C | $[\alpha]_D^{20}$ in ethanol |
|---|---|---|---|---|
| 3 | Piperidino- | Cl | 143–147° | +40° |
| 4 | Pyrrolidino- | Cl | 154–157° | +28° |
| 5 | Pyrrolidino- | Tartrate | 105–108° | +27° |
| 6 | Diisopropyl-amino | Cl | 165–167° | +34° |
| 7 | Diisopropyl-amino | Tartrate | 98–102° | +37° |
| 8 | Diisobutyl amino- | Cl | 145–147° | +35° |

The same compounds were prepared as identified in Examples 1–6 using in place of the solvent as therein described, a chlorinated hydrocarbon or acetonitrile.

The novel 21-deoxyhydroajmaline derivatives of the invention can be used in the form of tablets, dragees, powders and in the form of injectible solutions. Preferably the tablets and dragees contain from 20–100 mg/dragee of the active compound and the ampulles contain 10 – 20 mg/ml.

Most preferably, in the case of ampulle each ml of solution contains 15 mg of active compound.

What is claimed is:

1. A 21-deoxydihydroajmaline derivative having the formula

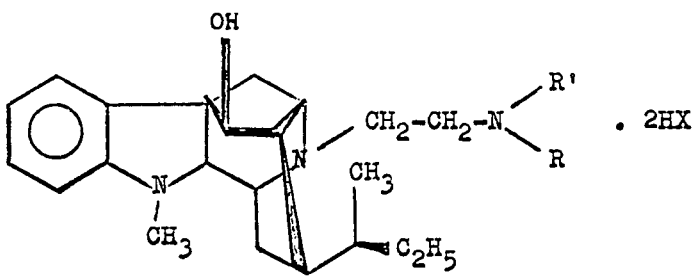 · 2HX wherein R and R' are each the same ethyl, isopropyl or isobutyl group or R and R' together with the N atom with which they are associated form a morpholino, piperidino or pyrrolidino ring; X is the anion of a physiologically acceptable inorganic or organic acid.

2. A compound according to claim 1, wherein the free base is designated 4-($\beta$-diethylaminoethyl)-deoxydihydroajmaline.

3. A compound according to claim 1, wherein the free base is designated 4-($\beta$-morpholinoethyl)-deoxydihydroajmaline.

4. A compound according to claim 1, wherein the free base is designated 4-($\beta$-piperidinoethyl)-deoxydihydroajmaline.

5. A compound according to claim 1, wherein the free base is designated 4-($\beta$-pyrrolidinoethyl)-deoxydihydroajmaline.

6. A compound according to claim 1, wherein the free base is designated 4-($\beta$-diisopropylaminoethyl)-deoxydihydroajmaline.

7. A compound according to claim 1, wherein the free base is designated 4-($\beta$-diisobutylaminoethyl)-deoxydihydroajmaline.

8. A therapeutic composition consisting essentially of a compound according to claim 1 in admixture with a pharmaceutically acceptable carrier.

9. A method of treating a subject having arhythmia comprising administering to such subject a therapeutically effective amount of a compound according to claim 1.

10. A method according to claim 9 wherein said compound is 4-($\beta$-morpholinoethyl)deoxydihydroajmaline.

* * * * *